(12) United States Patent
Foerner et al.

(10) Patent No.: US 9,161,731 B2
(45) Date of Patent: Oct. 20, 2015

(54) SUPPLY UNIT FOR A MOVABLE GANTRY

(71) Applicants: Ulrich Foerner, Ebensfeld (DE);
Christof Knoess, Forchheim (DE);
Markus Koerber, Buttenheim (DE);
Michael Loser, Forchheim (DE)

(72) Inventors: Ulrich Foerner, Ebensfeld (DE);
Christof Knoess, Forchheim (DE);
Markus Koerber, Buttenheim (DE);
Michael Loser, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 163 days.

(21) Appl. No.: 13/959,925

(22) Filed: Aug. 6, 2013

(65) Prior Publication Data
US 2014/0037071 A1 Feb. 6, 2014

(30) Foreign Application Priority Data

Aug. 6, 2012 (DE) .......................... 10 2012 213 875

(51) Int. Cl.
*A61B 6/00* (2006.01)
*A61B 6/03* (2006.01)

(52) U.S. Cl.
CPC . *A61B 6/44* (2013.01); *A61B 6/032* (2013.01); *A61B 6/4435* (2013.01); *A61B 6/4488* (2013.01)

(58) Field of Classification Search
CPC .............................. A61B 6/4405; A61B 6/035
See application file for complete search history.

(56) References Cited

U.S. PATENT DOCUMENTS

| 4,253,027 | A | * | 2/1981 | Taylor et al. .................... 378/14 |
| 5,305,363 | A | | 4/1994 | Burke et al. |
| 5,475,729 | A | | 12/1995 | Mattson et al. |
| 5,483,957 | A | * | 1/1996 | Janssen et al. ................ 378/194 |
| 7,887,237 | B2 | | 2/2011 | Krug |
| 2006/0274880 | A1 | | 12/2006 | Oikawa et al. |
| 2007/0195924 | A1 | | 8/2007 | Krumme |
| 2009/0147924 | A1 | | 6/2009 | Gross et al. |
| 2010/0150304 | A1 | | 6/2010 | Kawamura |
| 2012/0321050 | A1 | * | 12/2012 | Bouvier et al. ............... 378/194 |

* cited by examiner

*Primary Examiner* — Hoon Song
(74) *Attorney, Agent, or Firm* — Schiff Hardin LLP

(57) ABSTRACT

An imaging device has a gantry designed to movie along the floor of a room in which the imaging device is installed. The imaging device has a supply unit that includes a transfer arrangement to transfer power and/or data and/or coolant between a stationary supply source and the movable gantry. The supply unit is arranged in or on the floor.

4 Claims, 1 Drawing Sheet

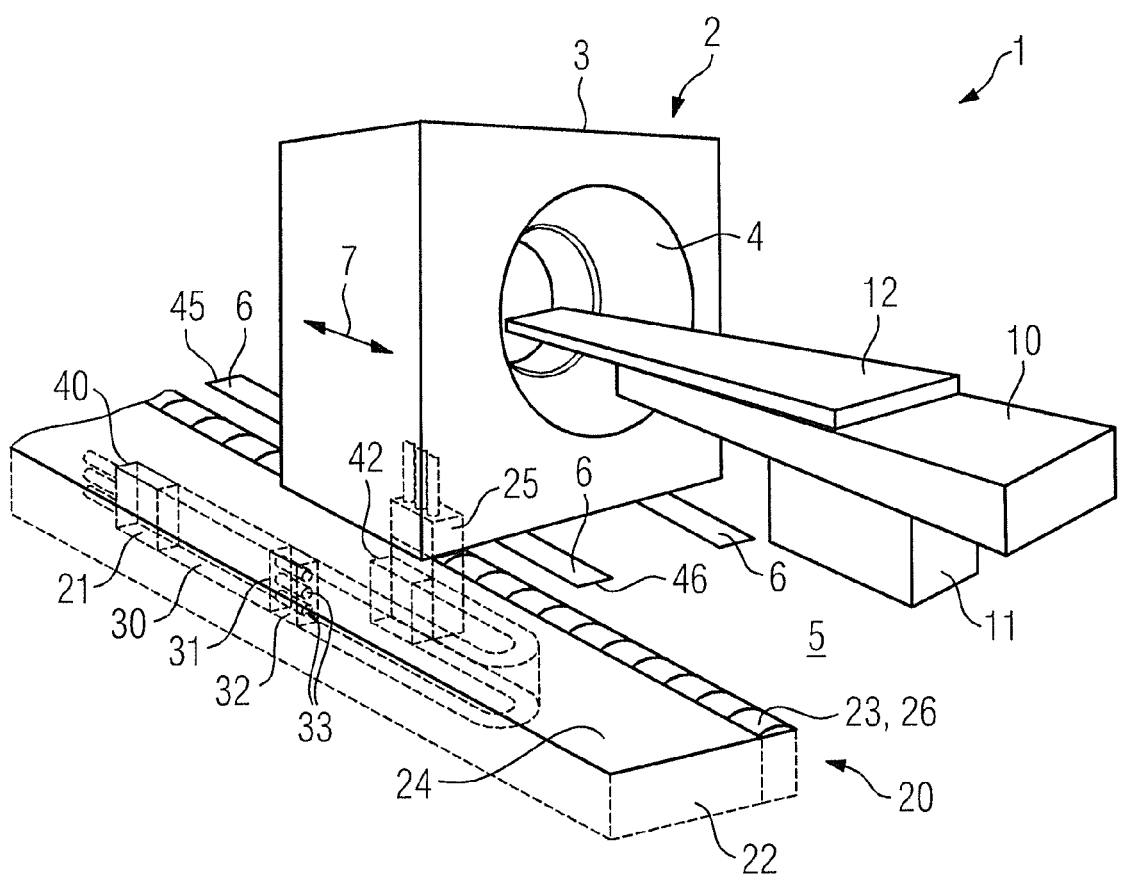

SUPPLY UNIT FOR A MOVABLE GANTRY

BACKGROUND OF THE INVENTION

1. Field of the Invention

The invention concerns a supply unit for a movable gantry of an image acquisition device, particularly a medical image acquisition device. The supply unit serves to transport power and/or data and/or coolant between the movable gantry and a stationary connection point (generally designated as a supply source in the following).

2. Description of the Prior Art

In the following, a movable gantry ("sliding gantry") means a structural unit that has at least one approximately annular housing (gantry) that is in penetrated by a tunnel, as well as components accommodated in the housing that enable an image acquisition. The entire gantry housing is movable, such as on rails recessed into the floor. For image acquisition purposes, the gantry is moved with respect to a patient bed associated with the gantry such that the bed is caused to protrude into the tunnel.

Such sliding gantries are presently used primarily in (x-ray) computed tomography systems (CT systems). An essentially annular mount (also designated as a ring collar) is supported inside the housing, on which mount are attached an x-ray source and a radially opposite x-ray detector. This mount rotates around the tunnel in a known manner to acquire slice images (tomograms) of a patient on the patient bed.

In a typical image acquisition method, projection images of a subject to be imaged (thus of the patient on the patient bed) are acquired slice-by-slice in a typical image acquisition method during successive feed of the gantry along the tunnel axis, and the projection images are electronically stored as image data. Finally, slice images or three-dimensional volume data sets of the subject to be imaged are calculated at a control and evaluation computer (associated with the gantry) by numerical back-projection of the acquired projection images. The acquisition of a series of projection images is also designated as a "scan" in the following.

Such a sliding gantry is frequently used in connection with an operation on the patient when an image acquisition is to take place in the course of the operation, and when a dedicated CT table cannot be used.

To operate the CT system, it is necessary to supply the sliding gantry with power and to transfer data (in particular image data acquired in a scan) as well as control signals between the gantry and the control and evaluation computer. In a liquid-cooled CT system, it is also necessary for a liquid coolant to be supplied to the gantry and discharged from it again.

In a conventional design, all conduits (for power, data and/or coolant) are directed from the gantry via a cable column into a component known as a ceiling module. The ceiling module is an (oblong) housing arranged near the ceiling (of an operating room, for example). This housing is arranged approximately parallel to the travel direction of the gantry. In the following, a device designated as a "power routing chain" is accommodated inside the housing.

Such a known power routing chain is a flexible module that directs and protects a conduit accommodated therein, and the power routing chain establishes a connection between the stationary supply source an a connection point with the gantry, whose location varies.

SUMMARY OF THE INVENTION

An object of the invention is to improve an imaging device with a sliding gantry with regard to data, power and coolant supply.

The imaging device according to the invention has a gantry that can be moved along the floor, as well as a supply unit. The supply unit has a transfer arrangement that transfers power and/or data and/or coolant between a stationary supply source and the sliding gantry. According to the invention, the supply unit is arranged in the region of the floor (in a preferred embodiment, in proximity to a travel region of the gantry).

"In the region of the floor" means that the supply unit is on the floor, but preferably is integrated, wholly or in part, into the floor. To avoid tripping at a bump that might be produced by the presence of the supply unit, the supply unit is preferably countersunk into the floor such that it terminates flush with the level of the floor.

In comparison to conventional imaging devices, the cable guide to the cover module that is described in the following, as well as the cover assembly itself, is forgone due to the arrangement of the supply unit in the floor, or at least near the floor. The imaging device according to the invention is characterized by a particularly compact structural shape of its components that are visible in the room. In addition to this, due to the omission of the cable column the gantry of the imaging device advantageously resembles an immobile gantry, which can, less an anxiety on the part of the patient. Since the cable column can be omitted according to the invention, collision problems with other modules that are possibly installed in the region of the column, such as ventilation systems, lamps, monitors etc., are precluded.

According to the invention, the supply unit can include at least one power supply unit and/or data supply unit for wireless transfer. However, the supply advantageously takes place via wires, with a power line and/or a data line and/or a coolant line being provided as a conduit.

The term "conduit" encompasses an electrical conduit such as an electrical cable (an electrical line) as well as a fluid conduit (in particular in the form of a hose).

In a preferred embodiment, the supply unit for hardwired supply of the gantry includes a power routing chain that is preferably produced from a stable plastic.

The power routing chain is essentially formed by a flexible, oblong hollow body to accommodate at least one conduit. A hollow body means an essentially hose-like body enclosing a free space, the wall of which body can either be of closed design or of interrupted design. In particular, the wall of the hollow body can optionally be opened along a longitudinal side (for insertion of the conduit) or be open in its original state.

In the installed state, a first longitudinal end of the power routing chain is associated with the supply source while a second longitudinal end of the power routing chain is associated with the gantry. In other words: a conduit accommodated by the power routing chain is connected at a first end with the supply source (so as to conduct electricity or a fluid) while the second end is connected with a connection point of the gantry (so as to conduct electricity or fluid).

In a preferred embodiment, multiple conduits are accommodated in the power routing chain, in particular in parallel or stranded with one another, for instance.

In an embodiment that is preferred in terms of servicing, the supply unit has a guide channel to accommodate the power routing chain, which is advantageously covered with a removable cover plate. The cover plate produces a tight seal with the surrounding floor. Additionally or alternatively, the guide channel is sealed at least in part with a cover (at a top side of the guide channel), which has a variable surface extent according to a travel movement of the gantry.

In a particularly compact embodiment, the supply unit is integrated into a rail directed in the floor which serves for movement of the gantry.

BRIEF DESCRIPTION OF THE DRAWINGS

The single FIGURE schematically illustrates a computed tomography system in accordance with the present invention.

DESCRIPTION OF THE PREFERRED EMBODIMENTS

The single FIGURE shows a computed tomography system (CT system) 1 serving as a medical image acquisition device. The CT system 1 serves to acquire slice images of a patient (not shown).

The CT system 1 has a computed tomography data acquisition unit essentially formed by a gantry 2.

The gantry has in a known manner, a housing 3 that surrounds rotatable assembly and that is penetrated by a tunnel opening 4.

The assembly (not shown) arranged inside the gantry 2 includes an annular mount (also designated as a rotating collar or ring) on which an x-ray source and an essentially radially opposite-ray detector are mounted. The x-ray detector detects a fan beam emanating from the x-ray source.

The gantry 2 is a movable ("sliding") gantry 2. For this purpose, the gantry 2 is designed so as to be capable of reversibly sliding in the arrow directions 7 on rails 6 that are attached to the floor 5 so as to be stationary.

In addition, the CT system 1 has a patient table 10 to support the patient. The patient table 10 has a base 11 attached so as to be stationary to the floor 5, on which base 11 a patient bed 12 is mounted so as to be capable of sliding. The patient table 10 is thereby positioned with regard to the gantry 2 so that the patient bed 12 protrudes into the tunnel opening 4 for image acquisition purposes when the gantry 2 is driven forward on the rails 6 as shown in the FIGURE (thus in the direction of the patient table 10).

The CT system 1 furthermore has a supply unit 20 with which the sliding gantry 2 is connected via wires to a stationary supply source 21 (shown only as an example).

The supply unit 20 has an oblong guide channel 22 that is recessed into the floor 5 in parallel with the travel direction of the gantry 2, for instance.

With the exception of a slot 23, the guide channel 22 is sealed with a cover plate 24 terminating flush with the surrounding floor 5. A connection finger 25 of the gantry 2 protrudes from above through the slot 23 into the guide channel 22. The slot 23 is sealed on both sides of the connection finger 25 with a telescoping cover 26 (made of stainless steel, for example) that adapts to the travel movement of the gantry 2.

A known, flexible power routing chain 30 is directed in the guide channel 22. The power routing chain 30 is produced essentially from a number of individual plastic elements 31 that move counter to one another, wherein each element 31 being essentially formed by a tube segment that is approximately rectangular in cross section. In the FIGURE, an element 31 is shown as an example. Overall, the power routing chain 30 encloses a free space 32 in which multiple conduits 33 are accommodated parallel to one another.

The conduits 33 here are a data line (executed as a coaxial cable, Ethernet cable or optical glass fiber), a power line (executed as an insulated copper line) and a coolant line (that, as an example, is executed as a plastic hose) to convey a (liquid or gaseous) coolant.

According to the FIGURE, a fixed end 40 of the power routing chain 30 is associated with the supply source 21 (meaning that the conduits 33 are connected at this point to respective, associated connection points of the supply source 21), while a free end 42 of the power routing chain 30 is associated with the connection finger 25 of the gantry 2. The conduits 33 are connected with respective associated connection point of the connection finger 25 at the region of the free end 42.

The power routing chain 30 is designed to feed the conduits 33 to the gantry 2 with protection and strain relief, both at a first end position of the gantry 2 (in which the gantry 2 is located approximately at the rear end 45 of the rails 6) and at a second end position of the gantry 2 (at the forward end 46 of the rails 6, and all points therebetween).

Although modifications and changes may be suggested by those skilled in the art, it is the intention of the inventors to embody within the patent warranted hereon all changes and modifications as reasonably and properly come within the scope of their contribution to the art.

We claim as our invention:

1. An imaging device comprising:
   an image data acquisition unit, comprising a gantry;
   a pair of rails installed on a floor of an installation room, with said gantry being linearly movable along said rails;
   a supply unit comprising a routing chain that transfers at least one of power, data and a coolant between a stationary supply source and said gantry;
   said supply unit comprising a guide channel in said floor proceeding parallel to said rails, and a routing chain in said guide channel, said routing chain comprising a flexible, oblong hollow routing chain body containing at least one conduit therein for hardwired supply of power to said gantry, said routing chain body comprising a first longitudinal end connected to said supply source and a second longitudinal end; and
   said supply unit comprising an opening in said floor allowing access into said channel, and said gantry comprising a connector that proceeds from said gantry through said opening and is connected to said second longitudinal end of said routing chain body in said channel, said connector moving along said opening as said gantry moves on said rails.

2. An imaging device as claimed in claim 1 wherein said routing chain comprises a plurality of conduits in said routing chain body.

3. An imaging device as claimed in claim 1 comprising a cover that at least partially covers said guide channel, said cover being adjustable to correspond to movement of said gantry along said guide channel.

4. An imaging device as claimed in claim 1 wherein said conduit is configured to transfer a supply commodity selected from the group consisting of power, data and coolant.

* * * * *